United States Patent [19]

Giani et al.

[11] Patent Number: 4,556,653

[45] Date of Patent: Dec. 3, 1985

[54] PYRIDO[1,5]BENZODIAZEPINONE DERIVATIVES AND PHARMACOLOGICAL ACTIVITIES THEREOF

[75] Inventors: Roberto Giani; Ettore Parini; Giancarlo Tonon, all of Milan, Italy

[73] Assignee: Dompe' Farmaceutica S.p.A., Milan, Italy

[21] Appl. No.: 609,100

[22] Filed: May 9, 1984

[30] Foreign Application Priority Data

May 17, 1983 [IT] Italy ............................. 21134 A/83

[51] Int. Cl.[4] ................... A61K 31/55; C07D 401/06; C07D 403/06; C07D 417/06
[52] U.S. Cl. ............................. 514/220; 260/239.3 T
[58] Field of Search ................. 260/239.3 T; 424/244, 424/270, 274, 263, 250; 422/256; 426/267; 514/220

[56] References Cited

U.S. PATENT DOCUMENTS

| | | | |
|---|---|---|---|
| 3,634,408 | 1/1972 | Schmidt et al. | 260/239.3 T |
| 3,660,380 | 5/1972 | Schmidt et al. | 260/239.3 T |
| 4,210,648 | 7/1980 | Schmidt et al. | 260/239.3 T |
| 4,213,984 | 7/1980 | Schmidt et al. | 260/239.3 T |
| 4,213,985 | 7/1980 | Schmidt et al. | 260/239.3 T |
| 4,377,576 | 3/1983 | Schmidt et al. | 260/239.3 T |
| 4,424,226 | 1/1984 | Eberlein et al. | 260/239.3 T |

Primary Examiner—Robert T. Bond
Attorney, Agent, or Firm—Walter H. Schneider

[57] ABSTRACT

11-Acyl derivatives of 5,11-dihydro-6H-pyrido-[2,3-b][1,4]benzodiazepin-6-one, 6,11-dihydro-5H-pyrido[2,3-b][1,5]benzodiazepin-5-one and 5,11-dihydro-6H-benzo[2,3-b][1,4]benzodiazepin-6-one, their preparation and pharmaceutical compositions endowed with antisecretory, antiulcer, antimuscarinic, spasmolytic activities containing the same, are described.

12 Claims, No Drawings

PYRIDO[1,5]BENZODIAZEPINONE DERIVATIVES AND PHARMACOLOGICAL ACTIVITIES THEREOF

The present invention refers to new compounds having general formula I

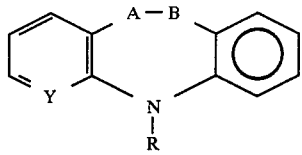

wherein Y is N or a CH group, A is NH and B is C=O or C=S or vice versa, R represents a group of formula

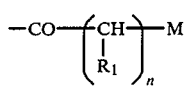

wherein:

$R_1$ represents hydrogen or $C_1-C_4$ linear or branched alkyl, n is 0, 1 or 2.

When n is 0, M represents one of the following nitrogen cyclic groups:

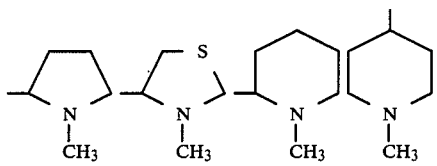

When n is 1 or 2, M is a group of formula:

wherein, when n is 1 and $R_1$ is hydrogen, $R_2$ represents hydrogen or $C_1-C_4$ linear or branched alkyl and $R_3$ is chosen among one of the following groups: —CH$_2$—CH=CH$_2$, —CH$_2$—C≡CH, CH$_2$—CH$_2$—CN,

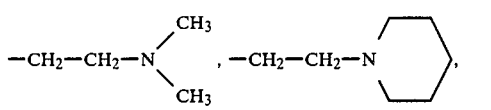

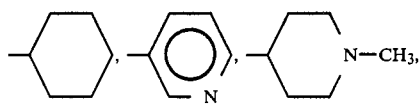

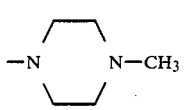

or $R_2$ and $R_3$, taken together, form one of the following cyclic residues:

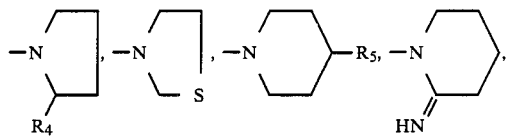

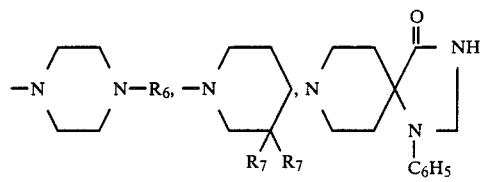

wherein $R_4$ is hydrogen, methyl or ethyl;

$R_5$ is —COOH, —COOCH$_3$, —COOC$_2$H$_5$ or

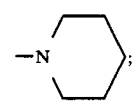

$R_6$ is acetyl, phenyl, cyclopropyl, CH$_2$—CH$_2$OH, CH$_2$—CH$_2$—CH$_2$OH, $$CH_2-\underset{OH}{CH}-CH_2OH,$$

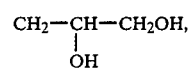 or

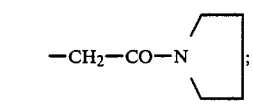

$R_7$ is hydrogen or methyl.

When n is 1 and $R_1$ is, on the other hand, $C_1-C_4$ alkyl, $R_2$ and $R_3$, separately, have the above mentioned meanings and, taken together, may form one of the following cycles:

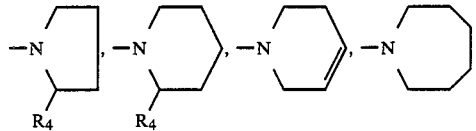

wherein $R_4$ has the above mentioned meaning.

Lastly, when n is 2, $R_1$ has the above mentioned meanings, $R_2$ may be hydrogen or methyl and $R_3$ represents one of the following groups:

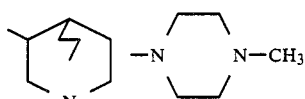

or $R_2$ and $R_3$, taken together, form one of the following cyclic residues:

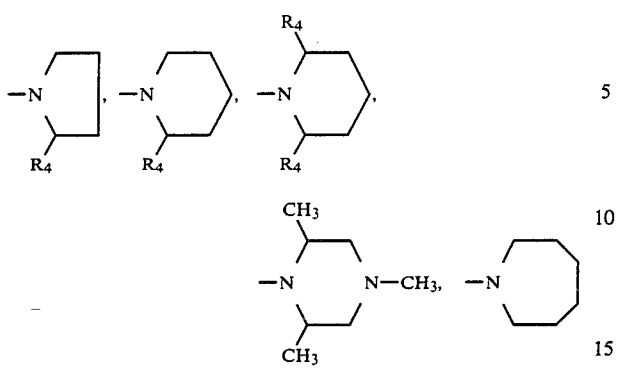

wherein R4 has the above mentioned meanings.

The compounds of formula I are endowed with interesting pharmaco-therapeutic properties, namely with antisecretory, antiulcer, spasmolytic and antimuscarinic activities. The invention therefore refers also to pharmaceutical compositions containing as the active principle one or more compounds of formula I or their pharmaceutically acceptable salts.

The invention refers also to a process for the preparation of the compounds of formula I.

Compounds I having n equal to to 0 are prepared starting from the compounds of formula II, described in the German Pat. No. 1,179,943, in Bull. Soc. Chim. Fran. 7, 2316, 1966 and in J. Med. Chem. 6, 255, 1963, by acylation with the acyl chlorides of formula III, according to the following scheme I:

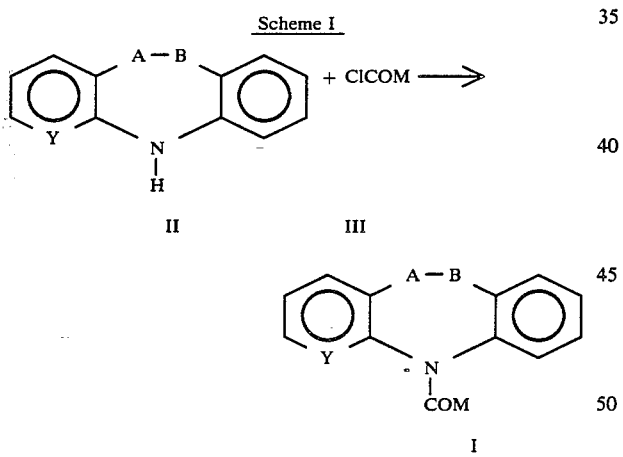

In the Scheme I, A, B, Y, M have the above mentioned meanings: M, when n=0, represents therefore the following groups:

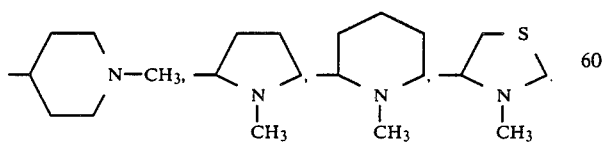

The reaction is carried out in polar solvents such as dimethylformamide, dimethylsulfoxide in the presence of bases such as triethylamine, alkaline hydroxides, alkaline carbonates at temperatures ranging from the room temperature and 150° C., with reaction times ranging from 2 to 24 hours.

The compounds I wherein n is, on the other hand, 1 or 2, are prepared by reaction of the chloroacyl derivatives IV, described in the German Pat. Nos. 1,795,183 and 2,724,478, in the French Pat. No. 1,505,795 and in J. Med. Chem. 6, 255, 1963 with amines of formula

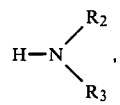

according to the following Scheme II:

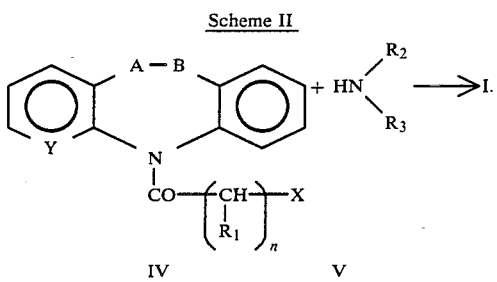

In the reported scheme, A, B, Y, n, $R_1$, $R_2$ and $R_3$ have the above seen meanings while X is an halogen atom.

The reaction is carried out in solvents such as benzene, alcohols, dioxane, etc. at temperatures ranging from the room temperature to the reflux temperature of the used solvent. As hydrohalogen acid binding base the amine V itself, an alkaline carbonate, triethylamine etc., may be used.

The reaction times are usually ranging from 2 to 24 hours.

The following examples further illustrate the invention, without limiting in any way the scope thereof.

EXAMPLE 1

11-[2-(Piperidin-1-yl)propionyl]-5,11-dihydro-6H-pyrido-[2,3-b][1,4]benzodiazepin-6-one A suspension of 11-(2-chloropropionyl)-5,11-dihydro-6H-pyrido[2,3-b][1,4]benzodiazepin-6-one (10 g) and piperidine (5.65 g) in benzene (350 ml) was refluxed with stirring for 20 hours. The reaction mixture was then cooled to room temperature and filtered, washing the collected solid with water.

Crystallization from 95° ethanol yielded 3.5 g (30.2%) of 11-[2-(piperidin-1-yl)propionyl]-5,11-dihydro-6H-pyrido[2,3-b][1,4]benzodiazepin-6-one melting at 238°-240° C. (dec.).

| | Microanalysis | |
|---|---|---|
| | Calc. % | Found % |
| C | 68.55 | 68.82 |
| H | 6.33 | 6.47 |
| N | 15.99 | 16.14 |

EXAMPLE 2

11-[2-(Hexamethylenimino)acetyl]-5,11-dihydro-6H-pyrido[2,3-b][1,4]benzodiazepin-6-one A suspension of 11-(2-chloroacetyl)-5,11-dihydro-6H-pyrido[2,3-b][1,4]benzodiazepin-6-one (15 g) and hexamethylenimine (10.34 g) in benzene (400 ml) was refluxed under stirring for 20 hours. The reaction mixture was then cooled to room temperature and filtered washing with water the collected solid. Crystallization from 95° ethanol yielded 8 g (43.8%) of 11-[2-(hexamethylenimino)acetyl]-5,11-dihydro-6H-pyrido[2,3-b][1,4]benzodiazepin-6-one melting at 199°–200° C.

|   | Microanalysis | |
|---|---|---|
|   | Calc. % | Found % |
| C | 68.55 | 68.33 |
| H | 6.33  | 6.54  |
| N | 15.99 | 15.75 |

EXAMPLE 3

11-(1-Methylpiperidin-4-carbonyl)-5,11-dihydro-6H-pyrido[2,3-b][1,4]benzodiazepin-6-one The chloride of 1-methylpiperidine-4-carboxylic acid hydrochloride (4.7 g) was added to a solution of 5,11-dihydro-6H-pyrido[2,3-b][1,4]benzodiazepin-6-one (5 g) and triethylamine (7.5 ml) in dimethylformamide (200 ml). The reaction mixture was heated to 90° C. for 24 hours.

The solvent was evaporated under vacuum and the residue was dissolved in 10% acetic acid (150 ml). The solution was repeatedly washed with methylene chloride, decolored with charcoal, alkalinized to pH 8 with saturated solution of sodium bicarbonate and extracted with methylene chloride (100 ml×5). The collected organic extracts were dried on sodium sulphate and evaporated. The residue, crystallized from ethanol-ethylether, yielded 2.4 g (30%) of 11-(1-methylpiperidin-4-carbonyl)-5,11-dihydro-6H-pyrido[2,3-b][1,4]benzodiazepin-6-one melting at 265°–267° dec.

|   | Microanalysis | |
|---|---|---|
|   | Calc. % | Found % |
| C | 67.84 | 67.81 |
| H | 5.99  | 6.08  |
| N | 16.65 | 16.53 |

EXAMPLE 4

11-[3-(Hexamethylenimino)propionyl]-5,11-dihydro-6H-pyrido[2,3-b][1,4]benzodiazepin-6-one A suspension of 11-(3-chloropropionyl)-5,11-dihydro-6H-pyrido[2,3-b][1,4]benzodiazepin-6-one (4.5 g) and hexamethylenimine (3.37 ml) in dioxane (50 ml) was refluxed under stirring for two hours. The reaction mixture was then cooled to room temperature and filtered. The collected solid was crystallized from 95° ethanol to give 3 g (55%) of 11-[3-(hexamethylenimino)propionyl]-5,11-dihydro-6H-pyrido[2,3-b][1,4]benzodiazepin-6-one melting at 217°–218° C.

|   | Microanalysis | |
|---|---|---|
|   | Calc. % | Found % |
| C | 69.21 | 69.42 |
| H | 6.64  | 6.73  |
| N | 15.37 | 15.20 |

EXAMPLE 5

11-[2-(2-Methylpiperidin-1-yl)acetyl]-6,11-dihydro-5H-pyrido[2,3-b][1,5]benzodiazepin-5-one A suspension of 11-(2-chloroacetyl)-6,11-dihydro-5H-pyrido[2,3-b][1,5]benzodiazepin-5-one (2.9 g) and 2-methylpiperidine (2.37 ml) in dioxane (30 ml) was refluxed under stirred for two hours. After cooling and filtration, the collected solid was crystallized from absolute ethanol to give 1.3 g (37.2%) of 11-[2-(2-methylpiperidin-1-yl)acetyl]-6,11-dihydro-5H-pyrido[2,3-b][1,5]benzodiazepin-5-one melting at 248°–249° C. (dec.).

|   | Microanalysis | |
|---|---|---|
|   | Calc. % | Found % |
| C | 68.55 | 68.35 |
| H | 6.33  | 6.17  |
| N | 15.99 | 15.68 |

EXAMPLE 6

11-[2-(4-Methylpiperazin-1-yl)acetyl]-5,11-dihydro-6H-pyrido[2,3-b][1,4]benzodiazepin-6-thione A suspension of 11-[2-(4-methylpiperazin-1-yl)acetyl]-5,11-dihydro-6H-pyrido[2,3-b][1,4]benzodiazepin-6-one dihydrochloride (10.6 g) and phosphorus pentasulfide (6.1 g) in pyridine (125 ml) was refluxed under stirring for 7 hours.

After cooling and filtration, the collected solid was suspended in chloroform (500 ml) and the suspension was repeatedly washed with saturated solution of sodium bicarbonate until disappearance of solid in suspension. The organic phase was dried on sodium sulphate and evaporated. The residue, crystallized first from acetonitrile and then from methanol, yielded 2.7 g (30%) of 11-[2-(4-methylpiperazin-1-yl)acetyl]-5,11-dihydro-6H-pyrido[2,3-b][1,4]benzodiazepin-6-thione melting at 240°–241° C.

|   | Microanalysis | |
|---|---|---|
|   | Calc. % | Found % |
| C | 62.10 | 62.32 |
| H | 5.76  | 5.84  |
| N | 19.06 | 19.06 |

EXAMPLE 7

11-[2-[4-(3-Hydroxypropyl)piperazin-1-yl]acetyl]-5,11-dihydro-6H-pyrido[2,3-b][1,4]benzodiazepin-6-one 1-Piperazinepropanol (8 g) was added to a suspension of 11-(2-chloroacetyl)-5,11-dihydro-6H-pyrido-[2,3-b][1,4]benzodiazepin-6-one (15 g) and anhydrous sodium carbonate (15 g) in absolute ethanol (250 ml).

The mixture was refluxed under stirring for 6 hours and then cooled. The salts were removed by filtration. The clear solution was evaporated to dryness and the residue, crystallized from acetonitrile, yielded 8.5 g (41%) of 11-[2-[4-(4-hydroxypropyl)piperazin-1-yl]acetyl]-5,11-dihydro-6H-pyrido[2,3-b][1,4]benzodiazepin-6-one melting at 215°–216° C.

|   | Microanalysis | |
|---|---|---|
|   | Calc. % | Found % |
| C | 63.78 | 63.62 |
| H | 6.37 | 6.41 |
| N | 17.70 | 17.64 |

EXAMPLE 8

11-(2-Chlorobutirryl)-5,11-dihydro-6H-pyrido[2,3-b][1,4]-benzodiazepin-6-one 2-Chlorobutirryl chloride (72.2 ml) was added to a suspension of 5,11-dihydro-6H-pyrido[2,3-b][1,4]benzodiazepin-6-one (100 g) and triethylamine (107 ml) in dioxane (1.9 lt.). The mixture was refluxed under stirring for 6 hours and then filtered still boiling. The filtrate was evaporated to dryness and the residue, crystallized from acetonitrile, yielded 60 g (40.2%) of 11-(2-chlorobutirryl)-5,11-dihydro-6H-pyrido[2,3-b][1,4]benzodiazepin-6-one melting at 207°–209° C.

|   | Microanalysis | |
|---|---|---|
|   | Calc. % | Found % |
| C | 60.86 | 60.84 |
| H | 4.47 | 4.47 |
| N | 13.31 | 13.28 |

EXAMPLES 9–52

Similarly to the previously described methods, but starting from the suitable intermediates, the compounds 9–52, whose formulae and chemico-physical characteristics are reported in the following Tables, were obtained.

TABLE I

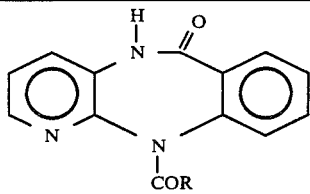

| Compound n. | R | Yield % | M.p. °C. | Calc. % C | Calc. % H | Calc. % N | Found % C | Found % H | Found % N |
|---|---|---|---|---|---|---|---|---|---|
| 9 | —CH₂N(CH₃)(CH₂CH₂CN) | 45 | 156–158 | 64.47 | 5.11 | 20.88 | 64.36 | 5.04 | 20.70 |
| 10 | —CH₂N(3,3-dimethylpiperidinyl) | 31 | 207–208 | 69.2 | 6.64 | 15.37 | 69.08 | 6.43 | 15.32 |
| 11 | —CH₂N(4-piperidinopiperidinyl)·HCl | 36 | 312–313 | 63.21 | 6.63 | 15.36 | 63.09 | 6.73 | 15.16 |
| 12 | —CH₂N(piperazinyl)N—CH₂CH₂OH | 29 | 212–214 | 62.98 | 6.08 | 18.36 | 62.78 | 5.90 | 18.16 |
| 13 | —CH₂N(piperazinyl)N—CH₂CH(OH)CH₂OH | 24 | 184–186 | 61.3 | 6.12 | 17.02 | 61.36 | 6.18 | 17.09 |
| 14 | —CH₂N(piperazinyl)N—COCH₃ | 28 | 284–286 | 63.31 | 5.58 | 1.46 | 63.38 | 5.71 | 18.22 |
| 15 | —CH₂N(piperazinyl)N—COOCH₂CH₃ | 51 | 213–214 | 61.60 | 5.66 | 17.10 | 61.86 | 5.72 | 17.11 |

TABLE I-continued
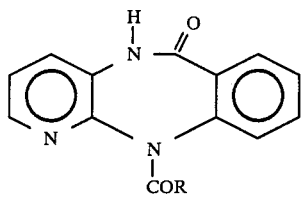
| Compound n. | R | Yield % | M.p. °C. | Calc. % C | Calc. % H | Calc. % N | Found % C | Found % H | Found % N |
|---|---|---|---|---|---|---|---|---|---|
| 16 | —CH₂N(piperazinyl)-C₆H₅ | 30 | 275 | 69.71 | 5.61 | 16.94 | 69.59 | 5.68 | 16.88 |
| 17 | —CH₂N(piperidinyl)-COOCH(CH₃)₂ | 33 | 202–203 | 65.39 | 6.20 | 13.26 | 65.42 | 6.27 | 13.30 |
| 18 | —CH(CH₃)-N(tetrahydropyridinyl) | 28 | 224–226 | 68.95 | 5.79 | 16.08 | 68.96 | 5.78 | 16.08 |
| 19 | —CH₂CH₂N(2,6-dimethylpiperidinyl) | 20 | 188–189 | 69.82 | 6.92 | 14.80 | 69.66 | 6.87 | 14.77 |
| 20 | —CH₂CH₂NH-(3-piperidinyl) | 24 | 207–209 | 67.50 | 6.44 | 17.89 | 67.60 | 6.45 | 17.86 |
| 21 | —CH-N(2-methylpiperidinyl) | 33 | 205–207 | 68.55 | 6.33 | 15.99 | 68.37 | 6.52 | 15.83 |
| 22 | —CH(CH₃)-N(pyrrolidinyl) | 57 | 224–226 | 67.84 | 5.99 | 16.65 | 67.91 | 6.02 | 16.58 |
| 23 | —CH₂N(spiro piperidinyl-hydantoin-N-C₆H₅) | 57 | 208–210 | 67.21 | 5.43 | 17.42 | 67.17 | 5.48 | 17.4 |
| 24 | —CH(CH₂CH₃)-N(piperazinyl)-N—CH₃·2HCl | 26 | 217–218 | 55.76 | 6.01 | 15.48 | 55.74 | 5.98 | 15.47 |

TABLE I-continued
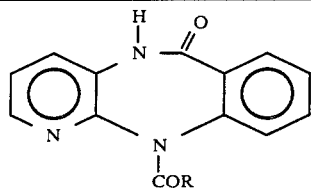
| Compound n. | R | Yield % | M.p. °C. | Microanalysis Calc. % C | H | N | Found % C | H | N |
|---|---|---|---|---|---|---|---|---|---|
| 25 | −CH−N⟨piperidine-2-CH₃⟩ / CH₃ | 35 | 238–239 | 69.21 | 6.64 | 15.37 | 69.11 | 6.60 | 15.35 |
| 26 | −CH−N⟨piperidine⟩ / CH₂CH₃ | 21 | 201–202 | 69.21 | 6.64 | 15.37 | 69.25 | 6.70 | 15.43 |
| 27 | −CH₂N⟨pyrrolidine-2-CH₃⟩ | 22 | 183–184 | 67.84 | 5.99 | 16.65 | 67.90 | 5.91 | 16.72 |
| 28 | −CH−N⟨pyrrolidine-2-CH₃⟩ / CH₃ | 29 | 186–187 | 68.55 | 6.33 | 15.99 | 68.51 | 6.40 | 16.06 |
| 29 | −CH₂N⟨piperidine-2-CH₂CH₃⟩ | 30 | 213–214 | 69.21 | 6.64 | 15.37 | 69.17 | 6.69 | 15.42 |
| 30 | −CH−N(CH₃)₂ / CH₃ | 26 | 208–210 | 65.79 | 5.84 | 18.05 | 65.90 | 5.69 | 18.08 |
| 31 | −CH−N(CH₃)−(piperazine-N−CH₃) / CH₃ | 48 | 181–182 | 67.15 | 6.91 | 17.80 | 67.24 | 6.94 | 17.72 |
| 32 | −CH₂−N(CH₃)−(piperazine-N−CH₃) | 20 | 175–177 | 66.47 | 6.64 | 18.45 | 66.51 | 6.58 | 18.44 |
| 33 | −CH₂−CH₂−N(CH₃)(cyclohexyl) | 22 | 183–184 | 69.82 | 6.92 | 14.80 | 69.74 | 6.92 | 14.78 |
| 34 | −CH−N(CH₃)(cyclohexyl) / CH₃ | 36 | 233–234 | 69.82 | 6.92 | 14.80 | 69.78 | 6.87 | 14.85 |

TABLE I-continued
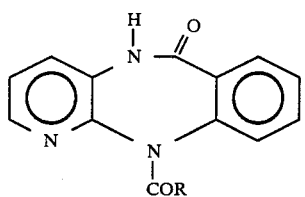
| Compound n. | R | Yield % | M.p. °C. | Calc. % C | Calc. % H | Calc. % N | Found % C | Found % H | Found % N |
|---|---|---|---|---|---|---|---|---|---|
| 35 | −CH₂−N(CH₂CH=CH₂)(cyclohexyl) | 26 | 209–211 | 70.75 | 6.71 | 14.35 | 70.81 | 6.70 | 14.37 |
| 36 | −CH₂−N(CH₃)(CH₂C≡CH) | 48 | 220–222 | 67.49 | 5.03 | 17.49 | 67.54 | 5.08 | 17.40 |
| 37 | −CH(CH₂CH₃)−N(pyrrolidine) | 23 | 227–228 | 68.55 | 6.33 | 15.99 | 68.48 | 6.27 | 16.04 |
| 38 | 3-methyl-1-methylpiperidine | 5 | 138–140 (dec.) | 67.84 | 5.99 | 16.65 | 67.98 | 6.11 | 16.74 |
| 39 | −CH(CH₂CH₃)−N(3,3-dimethylpiperidine) | 37 | 253–254 | 70.38 | 7.19 | 14.27 | 70.38 | 7.21 | 14.33 |
| 40 | −CH(CH₂CH₃)−N(4-piperidinopiperidine) | 15 | 138–140 | 69.77 | 7.43 | 15.65 | 69.82 | 7.41 | 15.58 |
| 41 | −CH₂CH₂−N(2-methylpyrrolidine) | 51 | 198–200 | 68.55 | 6.33 | 15.99 | 68.50 | 6.28 | 15.91 |

TABLE II
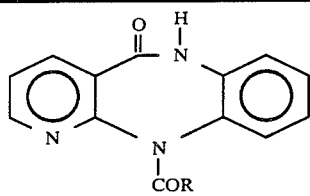
| Compound n. | R | Yield % | M.p. °C. | Calc. % C | Calc. % H | Calc. % N | Found % C | Found % H | Found % N |
|---|---|---|---|---|---|---|---|---|---|
| 42 | —CH₂N⟨pyrrolidine-CH₃⟩ | 50 | 245–247 | 67.84 | 5.99 | 16.65 | 67.82 | 5.94 | 16.70 |
| 43 | ⟨piperidine N—CH₃⟩ | 21 | 229–232 (dec.) | 67.84 | 5.99 | 16.65 | 67.79 | 6.04 | 16.73 |
| 44 | —CH₂CH₂N⟨piperazine N—CH₃⟩ | 41 | 189–191 | 65.74 | 6.34 | 19.16 | 65.88 | 6.22 | 19.15 |
| 45 | —CH(CH₃)—N⟨piperazine N—CH₃⟩.2HCl | 23 | 220–223 (dec.) | 54.80 | 5.75 | 15.98 | 54.96 | 5.91 | 16.11 |
| 46 | ⟨piperidine N—CH₃⟩ | 6 | 226–227 | 67.84 | 5.99 | 16.65 | 67.77 | 5.93 | 16.64 |
| 47 | —CH₂CH₂N⟨piperidine-CH₃⟩ | 33 | 158–160 | 69.21 | 6.64 | 15.37 | 69.23 | 6.70 | 15.39 |
TABLE III
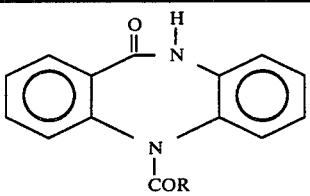
| Compound n. | R | Yield % | M.p. °C. | Calc. % C | Calc. % H | Calc. % N | Found % C | Found % H | Found % N |
|---|---|---|---|---|---|---|---|---|---|
| 48 | —CH₂N⟨pyrrolidine-CH₃⟩ | 21 | 170–172 | 71.62 | 6.31 | 12.53 | 71.60 | 6.33 | 12.58 |

TABLE III-continued

| Compound n. | R | Yield % | M.p. °C. | Microanalysis Calc. % C | H | N | Found % C | H | N |
|---|---|---|---|---|---|---|---|---|---|
| 49 | —CH₂CH₂—N(pyrrolidine with CH₃) | 51 | 169–170 | 72.18 | 6.63 | 12.02 | 72.26 | 6.54 | 11.95 |
| 50 | —CH₂CH₂—N(piperazine)N—CH₃ | 64 | 195–197 | 69.21 | 6.64 | 15.37 | 69.34 | 6.72 | 15.29 |
| 51 | —CH₂CH₂—N(CH₃)(cyclohexyl) | 30 | 152–154 | 73.18 | 7.21 | 11.13 | 73.02 | 7.15 | 10.98 |
| 52 | —CH₂—N(piperidine with 2,2-diCH₃) | 22 | 174–176 | 72.70 | 6.93 | 11.56 | 72.54 | 6.91 | 11.52 |

The antisecretory and anticholinergic activity in the rat, the acute toxicity in the mouse and the antimuscarinic activity, in comparison with pirenzepine as reference drug, have been determined on the compounds of the invention.

Gastric acid secretion in the pylorus ligated rat

The method of Shay H., Kamarov S. A., Fels, S. S., Meranee D., Gruenstein M., Siplet H., Gastroenterology, 5, 43 (1945) was used, slightly modified according to the following:

Male Sprague-Dawley rats weighing 150∓5 g fasting since 48 hours were used. Pylorus ligation was performed for 4 hours. The products under exam were administered by the oral route immediately after the ligation.

Carbachole salivation in the rat

The method cited by R. Turner: "Parasympatholytic Agents" in R. Turner "Screening Methods in Pharmacology" pag. 137. Academic Press. New York and London 1965, with slight changes, was used.

Male Sprague-Dawley rats, average weight 150∓5 g, fasting since 24 hours, were used.

The salivation was induced by the intraperitoneal administration of 1 mg/kg of carbachole.

The products under exam were administered orally one hour before the cholinergic stimulus.

Interaction with muscarinic receptor

The activity at the muscarinic receptor level was evaluated by means of displacement, with different concentrations of the compounds under exam, of the ³H-QNB bound to the receptors of the rat cerebral cortex according to the method, with minor changes, of H. I. Yamamura and S. H. Snyder-Proc. Nat. Acad. Sci., 71, 1725–1729 (1974).

Acute toxicity

The acute toxicity was determined by administering by oral route the substances under exam to Swiss mice; average weight 20∓2 g. The observation period was 14 days. 10 Animals were used for each tested dose.

The results are reported in the following Table IV.

TABLE IV

| | Pharmacological activities of the compounds I | | | | | | | |
|---|---|---|---|---|---|---|---|---|
| Compound n. | % Antisecretory activity mg/kg p.o | | | Carbachol salivation - % protection 62.5 mg/kg p.o. | Interaction with muscarinic receptor | | | $LD_{50}$ mg/kg p.o |
| | 6.25 | 12.5 | 25 | | $10^{-7}$ | $10^{-6}$ | $10^{-5}$ | |
| 1 | 10.3 | 36.3 | 71.3 | 0 | 0 | 3.96 | 46.6 | >500 |
| 2 | 11.6 | 33.7 | 55.2 | 100 | 12.8 | 49.7 | 93.3 | >500 |
| 4 | 21.5 | 50.2 | 64.1 | 50 | 3.0 | 54.3 | 94.4 | <500 |

TABLE IV-continued

| | Pharmacological activities of the compounds I | | | | | | | |
|---|---|---|---|---|---|---|---|---|
| Compound n. | % Antisecretory activity mg/kg p.o | | | Carbachol salivation - % protection 62.5 mg/kg p.o. | Interaction with muscarinic receptor | | | $LD_{50}$ mg/kg p.o |
| | 6.25 | 12.5 | 25 | | $10^{-7}$ | $10^{-6}$ | $10^{-5}$ | |
| 5 | 18.7 | 58.4 | 66.7 | 100 | 14.6 | 71.7 | 96.9 | <500 |
| 6 | 7.2 | 25.8 | 51.4 | 10 | 7.5 | 43.9 | 85.5 | <500 |
| 10 | 12.4 | 24.7 | 41.5 | 0 | 0 | 0.2 | 30.2 | >500 |
| P | 7.9 | 46.0 | 71.5 | 10 | 12.8 | 57.4 | 90.5 | >2000 |

P = Pirenzepine.

The present invention refers also to all the industrially applicable aspects connected with the use of compounds I in therapy.

An essential aspect of the invention is therefore provided by pharmaceutical compositions, suitable for the oral, parenteral or topical administration, containing as the active principle at least one of the compounds of formula I or one of pharmaceutically acceptable salts thereof in addition to the carriers usually employed in pharmaceutical technique.

Examples of said compositions are provided by capsules, sugar-coated tablets, tablets, syrups, drops, ointments, sterile vials for injection etc.

We claim:

1. A compound of the formula:

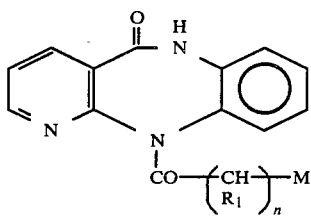

in which:
$R_1$ is H or $CH_3$
n is 0, 1 or 2
when:
n is 0
m represents a nitrogen cyclic group selected from:

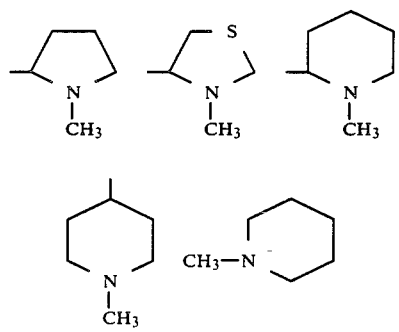

when:
n is 1 and $R_1$ is H
M represents a nitrogen cyclic group selected from:

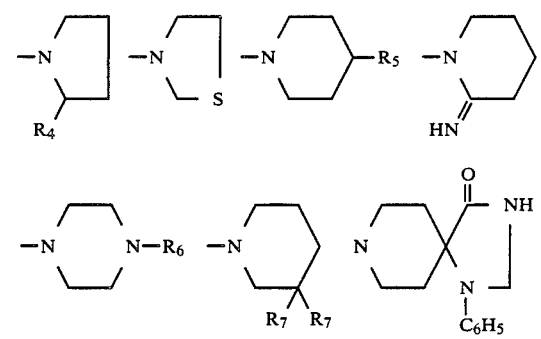

in which:
$R_4$ is H, $CH_3$ or $C_2H_5$
$R_5$ is —COOH, —COOCH$_3$, —COOC$_2$H$_5$ or

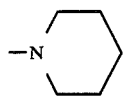

$R_6$ is acetyl, phenyl, cyclopropyl, $CH_2$—$CH_2OH$, $CH_2$—$CH_2$—$CH_2OH$,

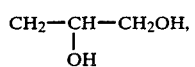

—COOC$_2$H$_5$ or

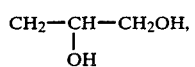

$R_7$ is H or $CH_3$
when:
n is 1 and $R_1$ is $CH_3$
M represents a nitrogen cyclic group selected from:

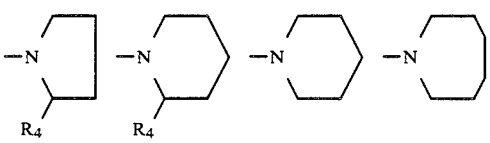

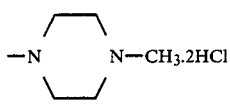

in which:
R₄ is H, CH₃ or C₂H₅
when:
n is 2 and R₁ is H
M represents a nitrogen cyclic group selected from:

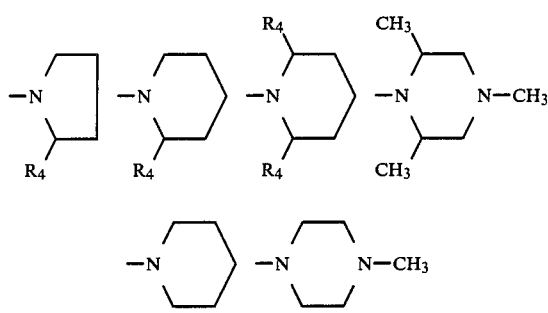

in which:
R₄ is H, CH₃ or C₂H₅.

2. A compound according to claim 1 in which n is 0.

3. A compound according to claim 2 in which the compound is 11-[(1-methyl-piperidine-4-yl)-carbonyl]-6,11-dihydro-5H-pyrido[2,3-b][1,5]-benzodiazepine-5-one.

4. A compound according to claim 2 in which the compound is 11-[(1-methyl-piperidine-3-yl)-carbonyl]-6,11-dihydro-5H-pyrido[2,3-b][1,5]-benzodiazepine-5-one.

5. A compound according to claim 1 in which n is 1.

6. A compound according to claim 5 in which the compound is 11-[(2-methyl-pyrrolidin-1-yl)-acetyl]-6,11-dihydro-5H-pyrido[2,3-b][1,5]-benzodiazepine-5-one.

7. A compound according to claim 5 in which the compound is 11-[2-(4-methyl-piperazine-1-yl)-propionyl]-6,11-dihydro-5H-pyrido[2,3-b][1,5]-benzodiazepine-5-one dihydrochloride.

8. A compound according to claim 1 in which n is 2.

9. A compound according to claim 8 in which the compound is 11-[3-(4-methyl-piperazine-1-yl)-propionyl]-6,11-dihydro-5H-pyrido[2,3-b][1,5]-benzodiazepine-5-one.

10. A compound according to claim 8 in which the compound is 11-[3-(2-methyl-piperidine-1-yl)-propionyl]-6,11-dihydro-5H-pyrido[2,3-b][1,5]benzodiazepine-5-one.

11. A pharmaceutical composition having antisecretory, antiulcer, antimuscarinic and spasmolytic activity which comprises as the principal active ingredient an effective amount of a compound according to claim 1, or a pharmaceutically acceptable salt thereof, together with a pharmaceutically acceptable carrier.

12. A pharmaceutical composition according to claim 11 in which the principal active ingredient is 11-[(1-methylpiperidine-4-yl)-carbonyl]-6,11-dihydro-5H-pyrido[2,3-b][1,5]-benzodiazepine-5-one.

* * * * *